United States Patent
Bampos et al.

[11] Patent Number: 6,013,055
[45] Date of Patent: Jan. 11, 2000

[54] CATHETER BALLOON HAVING SELECTED FOLDING CHARACTERISTICS

[75] Inventors: Pattiann Bampos, Wakefield; Ralph J. Barry, Hudson; Andrew J. Campbell, Reading; Bruce S. Hamilton, Lowell; Emmanuel Manetakis, Burlington, all of Mass.

[73] Assignee: Boston Scientific Corporation, Natick, Mass.

[21] Appl. No.: 08/969,904

[22] Filed: Nov. 13, 1997

[51] Int. Cl.[7] .................................................. A61M 29/00
[52] U.S. Cl. ................................................................ 604/96
[58] Field of Search .................................. 604/27, 30, 96, 604/104, 913, 915, 916, 920, 921; 606/191, 192, 194, 198

[56] References Cited

U.S. PATENT DOCUMENTS

| | | |
|---|---|---|
| 2,330,399 | 9/1943 | Winder . |
| 2,486,056 | 10/1949 | Oclassen . |
| 3,409,016 | 11/1968 | Foley . |
| 3,557,794 | 1/1971 | VanPatten . |
| 3,822,593 | 7/1974 | Oudewaal . |
| 4,018,231 | 4/1977 | Wallace . |
| 4,141,364 | 2/1979 | Schultze . |
| 4,178,939 | 12/1979 | Stephens . |
| 4,248,246 | 2/1981 | Ikeda . |
| 4,275,591 | 6/1981 | Wand . |
| 4,276,874 | 7/1981 | Wolvek et al. . |
| 4,292,974 | 10/1981 | Fogarty et al. . |
| 4,346,698 | 8/1982 | Hanson et al. . |
| 4,416,267 | 11/1983 | Garren et al. . |
| 4,444,186 | 4/1984 | Wolvek et al. . |
| 4,449,532 | 5/1984 | Storz . |
| 4,572,186 | 2/1986 | Gould et al. . |
| 4,573,470 | 3/1986 | Samson et al. . |
| 4,576,142 | 3/1986 | Schiff . |
| 4,592,744 | 6/1986 | Jagger et al. . |
| 4,601,713 | 7/1986 | Fuqua . |
| 4,636,201 | 1/1987 | Ambrose et al. . |
| 4,681,092 | 7/1987 | Cho et al. . |
| 4,711,181 | 12/1987 | Fuqua . |
| 4,738,666 | 4/1988 | Fuqua . |
| 4,743,258 | 5/1988 | Ikada et al. . |
| 4,762,125 | 8/1988 | Leiman et al. . |
| 4,762,130 | 8/1988 | Fogarty et al. . |
| 4,771,776 | 9/1988 | Powell et al. . |
| 4,796,629 | 1/1989 | Grayzel . |
| 4,820,349 | 4/1989 | Saab . |

(List continued on next page.)

FOREIGN PATENT DOCUMENTS

| | | |
|---|---|---|
| 0 414 350 A1 | 2/1991 | European Pat. Off. . |
| 0 414 350 B1 | 2/1991 | European Pat. Off. . |
| 1 170 586 | 5/1964 | Germany . |
| WO 92/19306 | 11/1992 | WIPO . |
| WO 95/00198 | 1/1995 | WIPO . |
| WO 95/05860 | 3/1995 | WIPO . |

*Primary Examiner*—Wynn Wood Coggins
*Assistant Examiner*—LoAn H. Thanh
*Attorney, Agent, or Firm*—Crompton, Seager & Tufte, LLC

[57] ABSTRACT

A balloon and method of manufacture for use in catheters for medical procedures, in particular percutaneous translumenal coronary angioplasty and other cardiovascular interventions. The balloon incorporates an inflatable membrane having a number of perpendicular ribs which have a higher resistance to collapse during deflation. A number of longitudinal ribs are provided which are preferably equidistantly spaced about a longitudinal axis and which extend between a proximal and distal end of the balloon. A number of triangular indentations are provided, wherein each triangular indentation is preferably equidistantly positioned between adjacent longitudinal ribs and each triangular indentation extends along a portion of the balloon between the proximal and distal ends. Each triangular indentation may extend through a perpendicular rib to reduce the resistance of the perpendicular rib to collapse during deflation. The number of triangular indentations enhance the collapse of the balloon from an expanded configuration to a folded configuration once the resistance of the number of perpendicular ribs to collapse has been overcome.

16 Claims, 5 Drawing Sheets

U.S. PATENT DOCUMENTS

| | | |
|---|---|---|
| 4,846,174 | 7/1989 | Willard et al. . |
| 4,846,344 | 7/1989 | Bala . |
| 4,846,801 | 7/1989 | Okuda et al. . |
| 4,881,547 | 11/1989 | Danforth . |
| 4,896,669 | 1/1990 | Bhate et al. . |
| 4,906,244 | 3/1990 | Pinchuk et al. . |
| 4,921,483 | 5/1990 | Wijay et al. . |
| 4,930,341 | 6/1990 | Euteneuer . |
| 4,935,190 | 6/1990 | Tennerstedt . |
| 4,938,676 | 7/1990 | Jackowski et al. . |
| 4,941,877 | 7/1990 | Montano, Jr. . |
| 4,994,072 | 2/1991 | Bhate et al. . |
| 5,015,230 | 5/1991 | Martin et al. . |
| 5,015,231 | 5/1991 | Keith et al. . |
| 5,017,325 | 5/1991 | Jackowski et al. . |
| 5,037,392 | 8/1991 | Hillstead . |
| 5,041,125 | 8/1991 | Montano, Jr. . |
| 5,087,246 | 2/1992 | Smith . |
| 5,147,302 | 9/1992 | Euteneuer et al. ................ 604/103 |
| 5,192,296 | 3/1993 | Bhate et al. . |
| 5,195,970 | 3/1993 | Gahara . |
| 5,196,024 | 3/1993 | Barath ................ 606/159 |
| 5,209,799 | 5/1993 | Vigil . |
| 5,226,887 | 7/1993 | Farr et al. . |
| 5,250,070 | 10/1993 | Parodi . |
| 5,254,091 | 10/1993 | Aliahmad et al. . |
| 5,295,995 | 3/1994 | Kleiman ................ 606/194 |
| 5,306,246 | 4/1994 | Sahatjian et al. . |
| 5,308,356 | 5/1994 | Blackshear, Jr. et al. . |
| 5,318,587 | 6/1994 | Davey . |
| 5,320,634 | 6/1994 | Vigil et al. ................ 606/159 |
| 5,336,178 | 8/1994 | Kaplan et al. ................ 604/53 |
| 5,336,472 | 8/1994 | Hillstead . |
| 5,342,301 | 8/1994 | Saab ................ 604/96 |
| 5,342,307 | 8/1994 | Euteneuer et al. . |
| 5,350,361 | 9/1994 | Tsukashima et al. . |
| 5,370,614 | 12/1994 | Amundson et al. . |
| 5,411,477 | 5/1995 | Saab . |
| 5,423,745 | 6/1995 | Todd et al. . |
| 5,456,666 | 10/1995 | Campbell et al. ................ 604/96 |
| 5,458,572 | 10/1995 | Campbell et al. ................ 604/96 |
| 5,470,313 | 11/1995 | Crocker et al. . |
| 5,478,319 | 12/1995 | Campbell et al. . |
| 5,490,839 | 2/1996 | Wang et al. . |
| 5,658,311 | 8/1997 | Baden ................ 606/192 |
| 5,718,684 | 2/1998 | Gupta ................ 604/96 |
| 5,853,389 | 12/1998 | Hijlkema ................ 604/96 |

CATHETER BALLOON HAVING SELECTED FOLDING CHARACTERISTICS

TECHNICAL FIELD

This invention relates to the field of medical devices, and more particularly, to the field of catheters such as balloon catheters having inflatable and collapsible balloons which are inserted into lumens of the human body, such as the arterial system to perform a variety of medical procedures. Specifically, the invention is directed to an improved balloon catheter incorporating a balloon shape which, during inflation, collapses to a low profile for improved catheter movement in the arterial system after a first inflation.

BACKGROUND OF THE INVENTION

The use of balloon catheters for treatment in the vascular system or other lumens of the body is well known in the field of medicine. Percutaneous transluminal angioplasty (PTA) is a procedure used for the treatment of the vascular system which opens blockages in the artery. One approach which has been used in the prior art for the treatment of blockages in arteries is a dilatation balloon catheter. The dilatation balloon catheter has an inflatable balloon member proximate a distal end which is positioned across a stenosis or blockage. The catheter is inserted into the vascular system and guided to position the balloon, whereupon a fluid is injected through an inflation lumen contained within the catheter to inflate the balloon. The inflation of the balloon causes an outward expansion which opens the stenosis.

It is desirable that the dilatation balloon have a low profile while deflated to increase the ease with which the dilatation balloon can be passed through arteries having small lumens and across a stenosis. The low profile is also desirable to minimize the force required to remove the balloon catheter. Thus, low range sheath withdrawal forces for balloon catheters has always been a desirable design goal.

One approach which has been used is to fold the balloon flat prior to a treatment such as PTA. This results in two wings being formed, which may be brought together in order to reduce the overall diameter of the preinflated balloon. A sleeve may be installed around the balloon in order to hold the wings together when the balloon is in the preinflated configuration. The balloon is inflated during treatment. Once the treatment is complete, the balloon must be deflated. Often times the deflated balloon does not return to a diameter small enough to fit within a guide catheter. Often times the result of deflating the balloon by pulling a vacuum is that the balloon can flatten in a phenomena known as "winging", in which the flat lateral portions of the deflated balloon extend outward beyond the diameter of the balloon when in its inflated and preinflated condition. The presence of the wings and edges can interfere with the ease of withdrawal, both through a guide catheter and through a body vessel such as an artery. Thus, a low profile upon deflation is desirable to increase the ease of retraction by decreasing contact with the vessel walls.

Several attempts have been made in the prior art to provide a dilatation balloon having a reduced profile when in a deflated state. Campbell et al. (U.S. Pat. No. 5,458,572) disclose a balloon having an array of longitudinally and circumferentially arranged ribs. The ribs are either more stiff or less stiff than a wall of the balloon. Upon evacuation of an inflation fluid from the balloon, either portions of the wall between the ribs will collapse between the ribs, or the ribs will collapse within the wall.

Campbell et al. (U.S. Pat. No. 5,456,666) disclose a balloon formed of a continuous balloon material which has a generally cylindrical shape and four ribs formed within a body. The ribs are longitudinally and equidistantly spaced about an axis which extends from the proximal end to the distal end of the balloon. The ribs are formed of stressed balloon material. Webs of less stressed balloon material are disposed between the ribs, whereupon the ribs and the webs form the balloon which is expandable from a folded condition to an expanded condition having a diameter substantially greater than the folded condition. After completion of a treatment, the balloon is reverted back to a folded condition where the webs between the ribs collapse inwardly towards the axis.

Montano (U.S. Pat. No. 4,941,877) discloses a balloon which defines transition zones at respective ends of the balloon which have flutes which are generally longitudinally directed at an angle to a balloon axis. The balloon can assume a collapsed position in which the collapsed transition zones collapse in a preferred cross section, rather than a flat collapsed configuration.

These prior art approaches attempt to improve the folding characteristics of the balloon by utilizing either longitudinally directed ribs within the mid region of the balloon, or by utilizing generally longitudinal fluted regions defined in the transition zones. The ribs or fluted regions attempt to induce the collapse of the balloon to a predetermined configuration by creating longitudinally oriented stressed regions in the balloon material.

SUMMARY OF THE INVENTION

The present invention overcomes the disadvantages of the prior art by providing a balloon catheter and method of manufacture which incorporates an inflatable balloon having a number of perpendicular ribs which have a high resistance to collapse during deflation. A number of longitudinal ribs are provided which are equidistantly spaced about a longitudinal axis and which extend between a proximal and distal end of the balloon. A number of triangular indentations are provided, wherein each triangular indentation is equidistantly positioned between adjacent longitudinal ribs and each triangular indentation extends along a portion of the balloon between the proximal and distal ends. Each triangular indentation may extend through a perpendicular rib to reduce the resistance of the perpendicular rib to collapse during deflation. The number of triangular indentations enhance the collapse of the balloon from an expanded configuration to a folded configuration because the triangular indentations along the rib weaken or lessen the resistance to folding along that rib. In this way, the resistance of the number of ribs to collapse has been overcome. In the folded configuration, the balloon has a low profile to minimize the balloon withdrawal force.

In a preferred embodiment, a balloon is provided which is formed of a flexible material which defines an inflation chamber which is adapted for inflation from a folded configuration to an expanded configuration, and deflation back to a preferred folded configuration. The balloon has a generally cylindrical shape about a longitudinal axis which extends between a proximal and distal end. In a preferred embodiment, the flexible material may be polyethylene terephthalate or any other suitable material. A number of longitudinal ribs are provided which are formed in the flexible material of the inflation chamber and which extend longitudinally between the proximal and distal end. The number of longitudinal ribs are equidistantly spaced about the longitudinal axis.

A number of perpendicular ribs can also be provided which are formed in the flexible material of the inflation chamber which intersect the number of longitudinal ribs. The number of perpendicular ribs are perpendicular to the longitudinal axis. The number of perpendicular ribs have a high resistance to collapse during deflation of the balloon.

In a preferred embodiment, a number of triangular indentations are provided which are formed in the flexible material of the inflation chamber, where each triangular indentation is equidistantly positioned between two adjacent ones of the number of longitudinal ribs. Each triangular indentation extends longitudinally a portion of the length between the proximal and distal end of the balloon. The number of triangular indentations enhance the collapse of the inflation chamber from the expanded configuration to the folded configuration once the resistance of the number of perpendicular ribs to collapse has been overcome. In a preferred embodiment, the total number of longitudinal ribs is four and the number of triangular indentations is four at each end of the balloon for a total of eight. In a preferred embodiment, the balloon comprises a reduced diameter or proximal transition region adjacent the proximal end, a reduced diameter distal transition region adjacent the distal end, and a body portion positioned between the proximal transition region and the distal transition region. In a preferred embodiment, the number of perpendicular ribs comprises a first plurality of the number of perpendicular ribs positioned in a first plane perpendicular to the longitudinal axis, where the first portion of the number of perpendicular ribs joins the proximal transition region to the proximal end body. The number of perpendicular ribs also comprises a second plurality of the number of perpendicular ribs positioned in a second plane perpendicular to the longitudinal axis, where the second portion of the number of perpendicular ribs joins the distal transition region to the distal end body. In a preferred embodiment, the first plurality of the number of perpendicular ribs is four and the second plurality of the number of perpendicular ribs is four. Each of the number of triangular indentations is an inwardly directed fold where the fold is directed towards the longitudinal axis and has a crease which is generally parallel to the longitudinal axis in a radial direction to the longitudinal axis.

In a preferred embodiment, a first portion of the number of triangular indentations is positioned near the proximal end of the balloon, where the crease of each one of the first portion of the number of triangular indentations extends through a particular one of the first plurality of the number of perpendicular ribs. A second portion of the number of triangular indentations is positioned near the distal end of the balloon, where the crease of each one of the second portion of the number of triangular indentations extends through a particular one of the second plurality of the number of perpendicular ribs. The crease of each one of the first portion of the number of triangular indentations extending through the particular one of the first plurality of the number of perpendicular ribs in addition to the crease of each one of the second portion of the number of triangular indentations extending through the particular one of the second plurality of the number of perpendicular ribs reduces the resistance of the number of perpendicular ribs to collapse during deflation and enhances the collapse of the inflation chamber from the expanded configuration to the folded configuration once the resistance of the number of perpendicular ribs to collapse has been overcome.

It is understood that within the scope of this invention are several embodiments which have triangular indentations located at any number of locations on the balloon. In an alternative embodiment of the present invention, a first portion of the number of triangular indentations is positioned within the proximal transition region where the crease of each one of the first portion of the number of triangular indentations extends from the proximal end of the balloon to a corresponding particular one of the first portion of the number of perpendicular ribs. The crease of each one of the first portion of the number of triangular indentations, however, does not extend through the corresponding particular one of the first plurality of the number of perpendicular ribs. A second portion of the number of triangular indentations is positioned within the distal transition region where the crease of each one of the second portion of the number of triangular indentations extends from the distal end of the balloon to a corresponding particular one of the second plurality of the number of perpendicular ribs. The crease of each one of the second portion of the number of triangular indentations, however, does not extend through the corresponding particular one of the second plurality of the number of perpendicular ribs. In this alternative embodiment, the crease of each one of the first portion of the number of triangular indentations, and the crease of each one of the second portion of the number of triangular indentations, enhance the collapse of the inflation chamber from the expanded configuration to the folded configuration once the resistance of the number of perpendicular ribs to collapse has been overcome.

In a second alternative embodiment, each one of the number of triangular indentations is positioned within the body portion of the balloon and the crease of each one of the number of triangular indentations extends from a proximal end to a distal end of the body. The crease of each one of the number of triangular indentations, however, does not intersect the corresponding particular one of the first plurality of the number of perpendicular ribs or the corresponding particular one of the second plurality of the number of perpendicular ribs. The crease of each one of the number of triangular indentations enhances the collapse of the inflation chamber from the expanded configuration to the folded configuration once the resistance of the number of perpendicular ribs to collapse has been overcome.

In a third alternative embodiment of the present invention, the crease of each one of the number of triangular indentations extends from a proximal end of the body to a distal end of the body. The crease of each one of the number of triangular indentations intersects and extends through a corresponding particular one of the first plurality of the number of perpendicular ribs and a corresponding particular one of the second plurality of the number of perpendicular ribs to reduce the resistance of the number of perpendicular ribs to collapse during deflation. The crease of each one of the number of triangular indentations enhances the collapse of the inflation chamber from the expanded configuration to the folded configuration once the resistance of the number of perpendicular ribs to collapse has been overcome.

In a fourth alternative embodiment, the crease of each one of the number of triangular indentations extends from the proximal end of the balloon to the distal end of the balloon. The crease of each one of the number of triangular indentations intersects the corresponding particular one of the first plurality of the number of perpendicular ribs and the corresponding particular one of the second plurality of the number of perpendicular ribs to reduce the resistance of the number of perpendicular ribs to collapse during deflation. The crease of each one of the number of triangular indentations enhances the collapse of the inflation chamber from the expanded configuration to the folded configuration once the resistance of the number of perpendicular ribs to collapse has been overcome.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figures 1, 2, 3, 4, 5, 6:
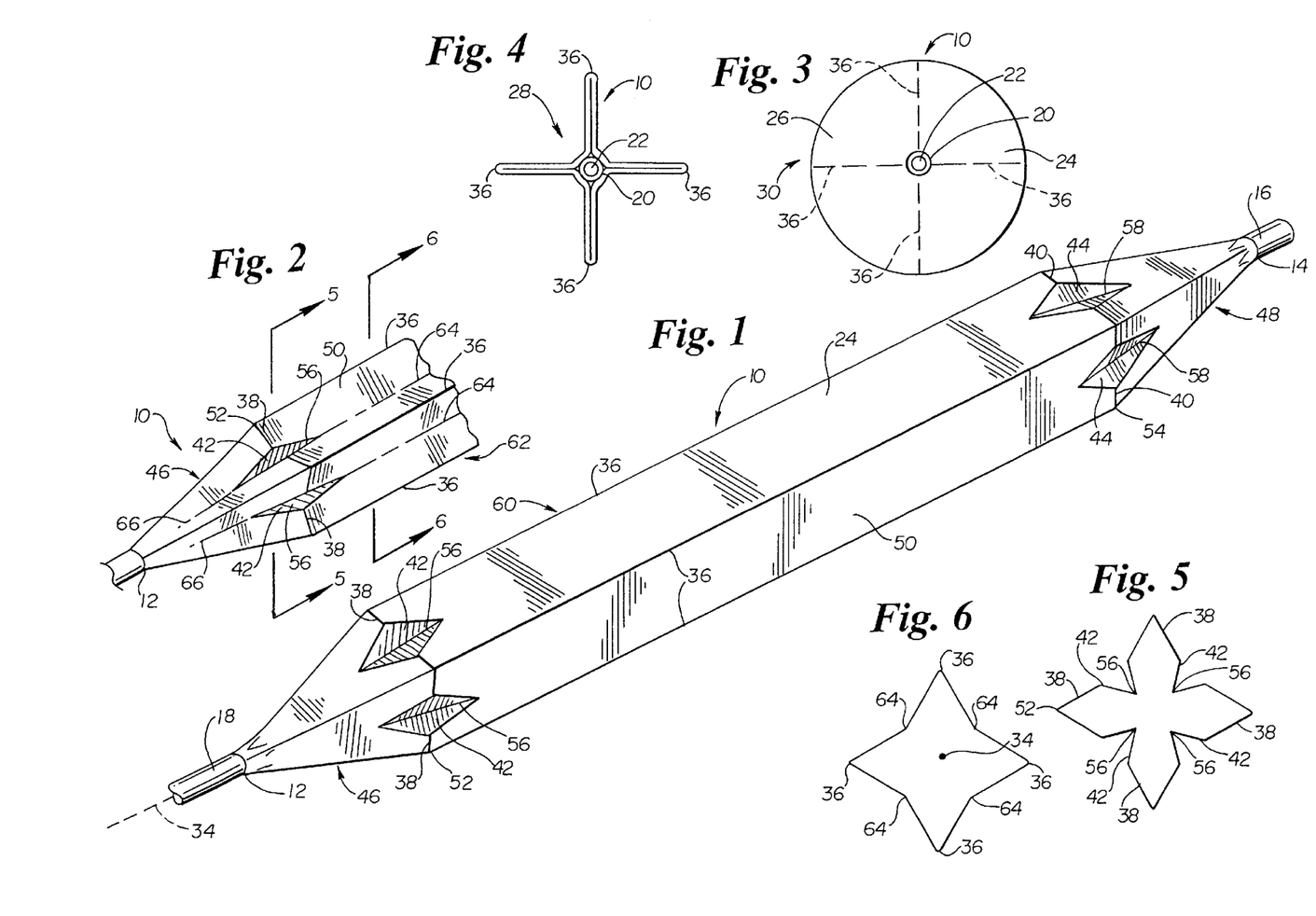
FIG. 1 is a perspective view of a balloon adapted to fold to a predetermined configuration in a preferred embodiment of the present invention.
FIG. 2 is a partial perspective view of an end of the balloon of FIG. 1 illustrating the collapse of the inflation chamber during deflation.
FIG. 3 is an end view of an inflated balloon showing the generally cylindrical shape of the balloon.
FIG. 4 is an end view of a deflated balloon showing a quad-folded configuration.
FIG. 5 is a cross-section view of the balloon of FIG. 2 taken along line 5—5 of FIG. 2.
FIG. 6 is a cross-section view of the balloon of FIG. 2 taken along line 6—6 of FIG. 2.

Referring now to the drawings, wherein like reference numerals refer to like elements throughout the several views, FIG. 1 is a perspective view of a balloon adapted to fold to a predetermined configuration in a preferred embodiment of the present invention. FIG. 1 illustrates generally a balloon 10 for a balloon catheter having a proximal end 12 and a distal end 14. Distal tip 16 is affixed at distal end 14. Shaft 18 couples to proximal end 12 of balloon 10. Shaft 18 also couples to a hub assembly (not shown). In the preferred embodiment, shaft 18 includes an inner shaft (not shown) disposed within outer shaft 18. The inner shaft extends through the length of the balloon from proximal end 12 through distal tip 16 to provide a guide wire lumen for guiding the balloon catheter over a guide wire (not shown). The annular space formed between the inner shaft and the outer shaft 18 forms an inflation lumen in fluid communication with balloon 10 to inflate and deflate balloon 10.

Balloon 10 is formed of a flexible material 24 which may be polyethylene terephthalate. The flexible material may also be a polyester ether block copolymer such as ARNITEL, available from DSM NV, Inc., or in the alternative, SELAR, available from DuPont. The balloon can be any polymeric material, such as polyamide, polyimide, polyethylene, liquid crystal polymer, polybutylone, terephthalate, or polyethylene naphthalate. Coextrusions of these materials are also possible. Flexible material 24 defines an inflation chamber 26 (see, FIG. 3). Balloon 10 is adapted for inflation from a deflated state 28 to an inflated state 30 (see, FIGS. 4 and 3, respectively). The expanded configuration shown in FIG. 3 has a generally cylindrical shape indicating a fully inflated balloon, while the balloon of FIG. 1 is shown partially inflated to detail its molded shape.

A longitudinal axis 34 extends between proximal end 12 and distal end 14. Longitudinal ribs 36 are formed in flexible material 24 of balloon 10 and extend longitudinally from proximal end 12 and distal end 14. The term ribs is used herein to define an angle transition or change on the longitudinal surface of the balloon. In FIG. 1, this angle change is 90°. Longitudinal ribs 36 are equidistantly spaced about longitudinal axis 34. Proximal perpendicular ribs 38 and distal perpendicular ribs 40 intersect with longitudinal ribs 36. Perpendicular ribs 38 and perpendicular ribs 40 are perpendicular to longitudinal axis 34. Perpendicular ribs 38 and perpendicular ribs 40 have a higher resistance to collapse during deflation of balloon 10.

Proximal triangular indentations 42 and distal triangular indentations 44 are formed in flexible material 24 of balloon 10. Each proximal triangular indentation 42 is equidistantly positioned between two adjacent ones of proximal longitudinal ribs 36 and extends longitudinally at least a portion of the length between proximal end 12 and distal end 14. Each distal triangular indentation 44 is equidistantly positioned between two adjacent ones of distal longitudinal ribs 36 and extends longitudinally at least a portion of the length between proximal end 12 and distal end 14. Triangular indentations 42 and triangular indentations 44 enhance the collapse of inflation chamber 26 from inflated state 30 to deflated state 28 once the resistance of perpendicular ribs 38 and perpendicular ribs 40 to collapse has been overcome as balloon 10 is deflated. It is believed the triangular indentations are stress concentrations that interrupt the natural resistance associated with the perpendicular ribs. They create a weak spot or stress concentration that serves as a hinge for the perpendicular rib to collapse.

Balloon 10, as shown in FIG. 1, has four longitudinal ribs 36, four proximal perpendicular ribs 38 and four distal perpendicular ribs 40. Balloon 10 further comprises a reduced diameter proximal transition region 46 adjacent proximal end 12, a reduced diameter distal transition region 48 adjacent distal end 14, and a body 50 positioned between proximal transition region 46 and distal transition region 48. Perpendicular ribs 38 are positioned in a first plane 52 which is perpendicular to longitudinal axis 34, wherein perpendicular ribs 38 join proximal transition region 46 to body 50. Perpendicular ribs 40 are positioned in a second plane 54 which is perpendicular to longitudinal axis 34, wherein perpendicular ribs 40 join distal transition region 48 to body 50. Perpendicular ribs 38 comprise four perpendicular ribs which intersect longitudinal ribs 36. Perpendicular ribs 40 comprise four perpendicular ribs which intersect longitudinal ribs 36. Triangular indentations 42 and triangular indentations 44 are each inwardly directed folds, wherein each fold is directed towards longitudinal axis 34. Each triangular indentation 42 has a crease 56 and each triangular indentation 44 has a crease 58. Crease 56 and crease 58 extend longitudinally at an angle radially toward longitudinal axis 34.

FIG. 2 is a partial perspective view of an end of the balloon of FIG. 1. FIG. 2 shows generally the proximal transition region 46 and a portion of body 50 of FIG. 1 to illustrate the quad-folding nature of balloon 10 as balloon 10 is deflated from an inflated state 30 to a deflated state 28. Balloon 10 can exist in a variety of different stages of inflation. The fully pressurized state of inflation is shown in FIG. 3. FIG. 1 shows balloon 10 in a relaxed or non-pressurized state 60. FIG. 2 shows balloon 10 in a partially depressurized or partially deflated state 62. FIG. 4 shows balloon 10 in a deflated state 28 in which balloon 10 is in a quad-folded configuration. FIG. 2 shows triangular indentations 42 positioned near proximal end 12 of balloon 10, wherein creases 56 of triangular indentations 42 extend through perpendicular ribs 38. When balloon 10 begins to be deflated under vacuum and goes from a non-pressurized state 60 to a partially depresessurized state 62, creases 56 extending through perpendicular ribs 38 are further extended outside of triangular indentations 42 both into body 50 as creases 64 and into proximal transition region 46 as creases 66. As balloon 10 is deflated from non-pressurized state 60 to partially depressurized state 62, triangular indentations 42 extending through perpendicular ribs 38 reduce the resistance of perpendicular ribs 38 to collapse during deflation in order that creases 56 may extend into body 50 (see, creases 64) and into proximal transition region 46 (see, creases 66). This enhances the collapse of inflation chamber 26 of balloon 10 from the expanded configuration shown as inflated state 30 to the folded configuration shown as deflated state 28 once the resistance of perpendicular ribs 38 to collapse has been overcome by deflation.

FIG. 3 is an end view of an inflated balloon showing the generally cylindrical shape of the balloon. FIG. 3 shows balloon 10 in the expanded configuration or inflated state 30 in which balloon 10 has a generally cylindrical shape. To achieve the inflated state, an inflation fluid applied under pressure causes balloon 10 to expand to a level of pressurization where longitudinal ribs 36 become less pronounced. FIG. 3 illustrates inner shaft 20 and guide wire lumen 22. In operation, balloon 10 in a deflated state 28 may be inserted across a tight stenosis wherein subsequent pressurization increases the diameter of balloon 10 as shown by inflated state 30. Once the inflation fluid is withdrawn under vacuum, balloon 10 deflates to the quad-folded configuration or deflated state 28 shown in FIG. 4.

FIG. 4 illustrates that once inflation fluid has been withdrawn under vacuum, balloon 10 refolds into a quadra-folded configuration to minimize patient trauma during withdrawal. The patient trauma is minimized by minimizing the profile of balloon 10. FIGS. 5 and 6 illustrate how triangular indentations 42 in combination with longitudinal ribs 36 and perpendicular ribs 38 achieve this quadra-fold configuration which minimizes the profile of balloon 10.

FIG. 5 is a cross-sectional view of the balloon of FIG. 2 taken along line 5—5 of FIG. 2. The plane of 5—5 of FIG. 2 is also first plane 52. FIG. 5 shows creases 56 of triangular indentations 42 extending through perpendicular ribs 38 to reduce the resistance of perpendicular ribs to collapse during deflation resulting in creases 56 extending into body 50 (see, creases 64) and into proximal transition region 46 (see, creases 66). Perpendicular ribs 38 provide rigidity to allow the transfer of creases 56 into body 50 and proximal transition region 46 so that once the perpendicular resistance to collapse has been broken or reduced, creases 56 extending into body 50 and proximal transition region 46 will enhance and further induce the quad-folding nature of balloon 10.

FIG. 6 is a cross-sectional view of the balloon of FIG. 2 taken along line 6—6 of FIG. 2. FIG. 6 shows balloon 10 in a partially depressurized state 62, wherein creases 64 have transferred from triangular indentations 42 into body 50. Creases 64 have enhanced and induced the quad-folding nature of balloon 10 by drawing in towards longitudinal axis 34 as balloon 10 is deflated to deflated state 28.

Figure 7:
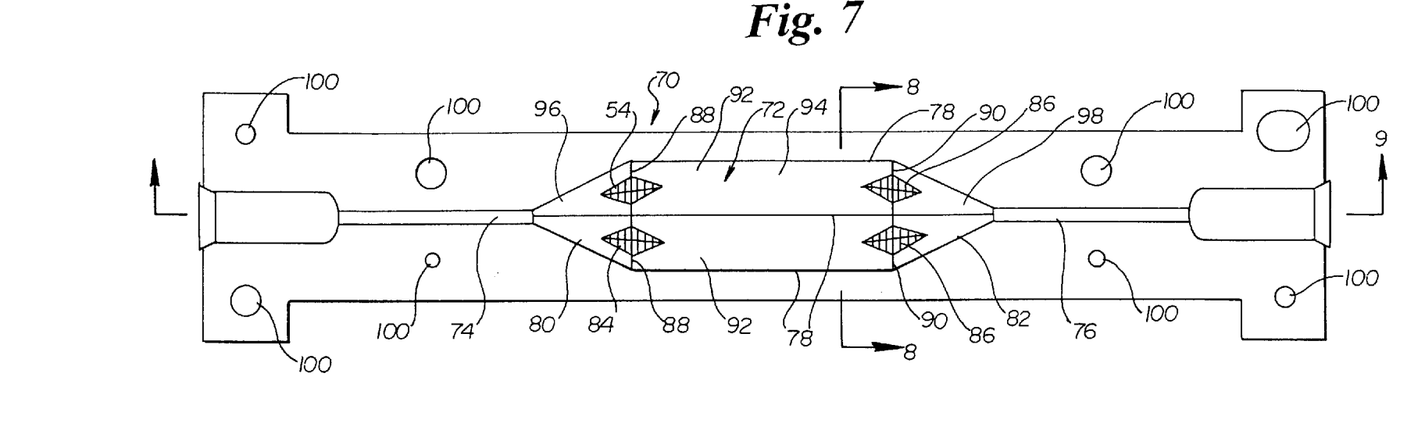
FIG. 7 is a plan view of one half of a mold for forming the balloon of a preferred embodiment.

FIG. 7 is a plan view of one-half of a mold for forming the balloon of a preferred embodiment. Mold casing 70 shown in FIG. 7 has a cavity 72 for receiving the balloon material. Cavity 72 has corners 78 corresponding to longitudinal ribs 36. It is understood that the half of the mold casing not shown is symmetrical in construction to mold casing 70 and thus not described. Cavity 72 also has end 80 and end 82. End 80 corresponds with proximal transition region 46 and end 82 corresponds with distal transition region 48. Protrusions 84 correspond with triangular indentations 42 and protrusions 86 correspond with triangular indentations 44. Edges 88 correspond to perpendicular ribs 38 and edges 90 correspond to perpendicular ribs 40.

Mold casing 70 is coupled to its mating half so that a cavity is formed having four corners 78 and four side walls 92. Corners 78 form a 90° angle with opposing side walls 92 in body region 94, proximal region 96 and distal region 98. Thus, once balloon 10 is positioned within cavity 72 and mold casing 70 is coupled to its mating half via mounting apparatus 100, a polymeric material is injected inside to expand balloon 10 until flexible material 24 is urged against the interior of cavity 72. Preferably with heat being applied to the mold to maintain fluidity and shape flexible material 24, corners 78 form longitudinal ribs 36, edges 88 form perpendicular ribs 38, edges 90 form perpendicular ribs 40, protrusions 84 form triangular indentations 42 and protrusions 86 form triangular indentations 44. Mold casing 70 in combination with its mating half form four longitudinal ribs 36, four perpendicular ribs 38, four perpendicular ribs 40, four triangular indentations 42, and four triangular indentations 44, all of which enhance and induce the quadra-folding nature of balloon 10 into the quadra-folded configuration or deflated state 28.

Figure 8:
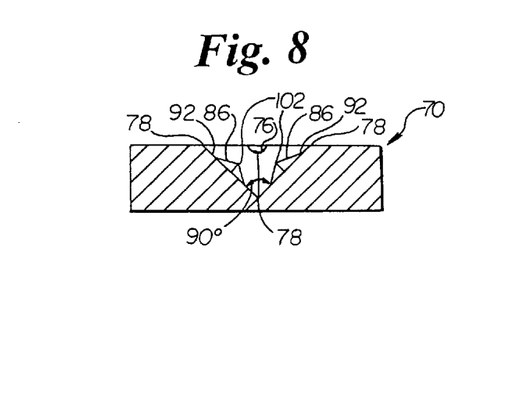
FIG. 8 is a cross-sectional view of the mold of FIG. 7 taken along line 8—8 of FIG. 7.

FIG. 8 is a cross-sectional view of the mold of FIG. 7 taken along line 8—8 of FIG. 7. Mold casing 70 shown in FIG. 8 has a 90° angle between opposing side walls 92. Protrusions 86 extend above side walls 92 so that edges 88 may form creases 56.

Figure 9:
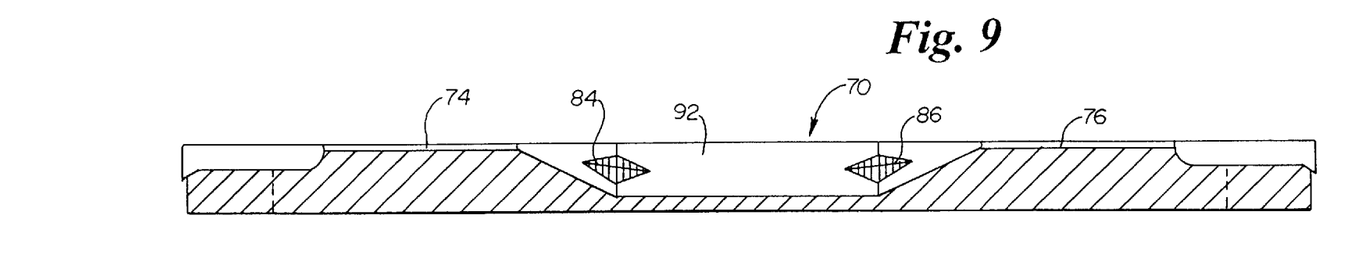
FIG. 9 is a cross-section view of the mold of FIG. 7 taken along line 9—9 of FIG. 7.

FIG. 9 is a cross-sectional view of the mold of FIG. 7 taken along line 9—9 of FIG. 7. FIG. 9 shows a view of cavity 72 rotated 45° along longitudinal axis 34 to illustrate the symmetrical relationship of side walls 92. As shown in FIG. 8, opposing side walls 92 create 90° angles therebetween to form the balloon 10 of FIG. 1.

Figures 10, 11:
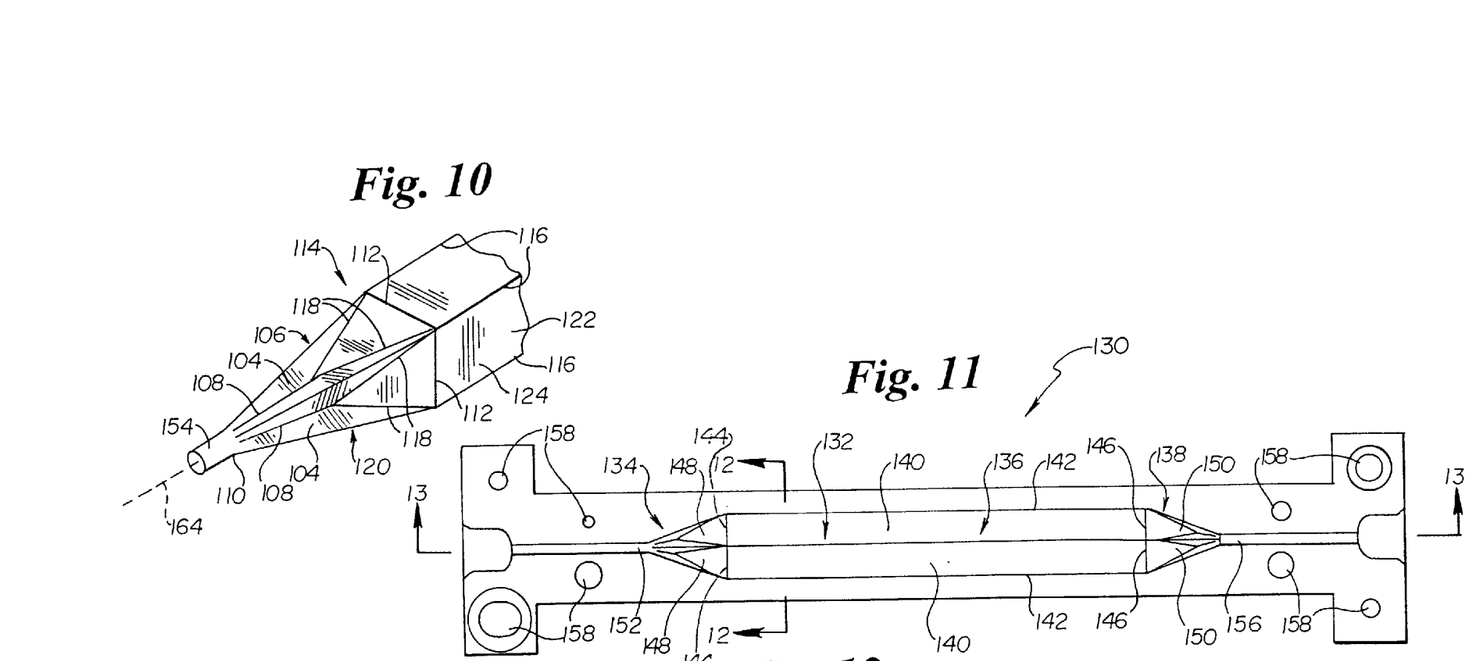
FIG. 10 is a perspective view of an end of a balloon showing an alternative embodiment of the present invention.
FIG. 11 is a plan view of one half of a mold for forming the balloon of an alternative embodiment.

FIG. 10 is a perspective view of an end of a balloon showing an alternative embodiment of the present invention. FIG. 10 shows triangular indentations 104 positioned within proximal transition region 106 of balloon 114. Creases 108 of triangular indentations 104 extend from proximal end 110 to an adjacent corresponding one of perpendicular ribs 112. Balloon 114 has longitudinal ribs 116 positioned as in balloon 10 of FIG. 1. Since creases 108 do not intersect perpendicular ribs 112, creases 118 are formed within proximal transition region 106 to join creases 108 to longitudinal ribs 116 to enhance the quad-folding nature of balloon 114.

The alternative embodiment shown in FIG. 10 has a distal transition region, not shown, which is shaped similarly to proximal transition region 106 and is thus not described. Balloon 114 is shown in a non-pressurized state 120. When balloon 114 is deflated to the quad-folded configuration in deflated state 28 shown in FIG. 4, creases 108 enhance the collapse of inflation chamber 122 of balloon 114 from an expanded configuration or inflated state 30 to a quad-folded configuration of deflated state 28 by extending creases 108 through perpendicular ribs 112 once the resistance of perpendicular ribs 112 to collapse has been overcome during deflation. Creases 108 then extend to body 124 between longitudinal ribs 116 to induce the refolding of balloon 114 into deflated state 28 as shown in FIG. 4.

FIG. 11 is a plan view of one half of a mold for forming the balloon of the alternate embodiment. FIG. 11 shows half of a mold casing 130. The half of the mold casing 130 shown in FIG. 11 is symmetrical with respect to the features of balloon 114 in FIG. 10 in comparison to the other half of the mold casing which is not shown. Thus, only mold casing 130 is described herein. Cavity 132 of mold casing 130 has proximal region 134, body region 136, and distal region 138. In cavity 132, side walls 140 are opposing at a 90° angle. Corners 142 correspond to longitudinal ridges 116. Proximal region 134 has edges 144 which correspond to perpendicular ribs 112. Distal region 138 has edges 146. Proximal region 134 has protrusions 148 which correspond to triangular indentations 104. Distal region 138 has protrusions 150. Mounting apparatus 158 are used to attach mold casing 130 shown in FIG. 11 to the other half which is not shown.

Figure 12:
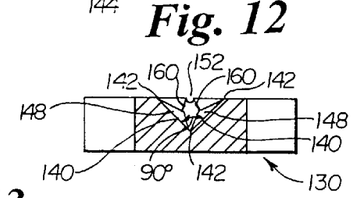
FIG. 12 is a cross-section view of the mold of FIG. 11 taken along line 12—12 of FIG. 11.

FIG. 12 is a cross-sectional view of the mold of FIG. 11 taken along line 12—12 of FIG. 11. FIG. 12 shows protrusions 148 which correspond to triangular indentations 104. Side walls 140 are shown opposing at a 90° angle. Ridges 160 correspond to creases 108 as shown extending up to channel 152. FIG. 12 also illustrates corners 142 which correspond to longitudinal ribs 116.

Figure 13:
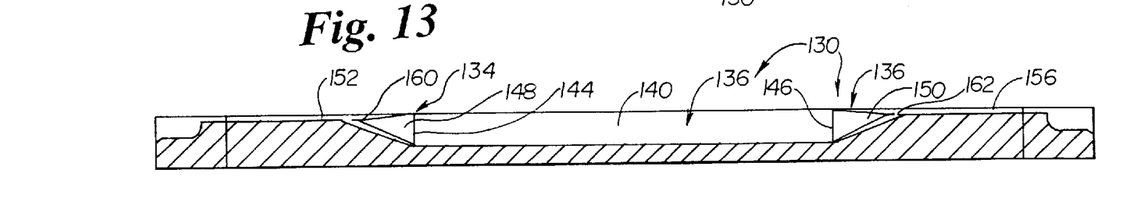
FIG. 13 is a cross-section view of the mold of FIG. 11 taken along line 13—13 of FIG. 11.

FIG. 13 is a cross-sectional view of the mold of FIG. 11 taken along line 13—13 of FIG. 11. FIG. 13 shows side walls 140 of body region 136 and proximal region 134 and distal region 138. Proximal region 134 has edge 144 which corresponds to perpendicular ribs 112. Distal region 136 has edge 146. Protrusion 148 of proximal region 134 corresponds to triangular indentation 104. Rib 160 corresponds with crease 108 and is shown extending up to channel 152. Distal region 136 has rib 162. The view shown in FIG. 13 along line 13—13 of FIG. 12 illustrates that cavity 132 and balloon 114 are symmetrical with respect to a 45° rotation along longitudinal axis 164.

Figure 14:
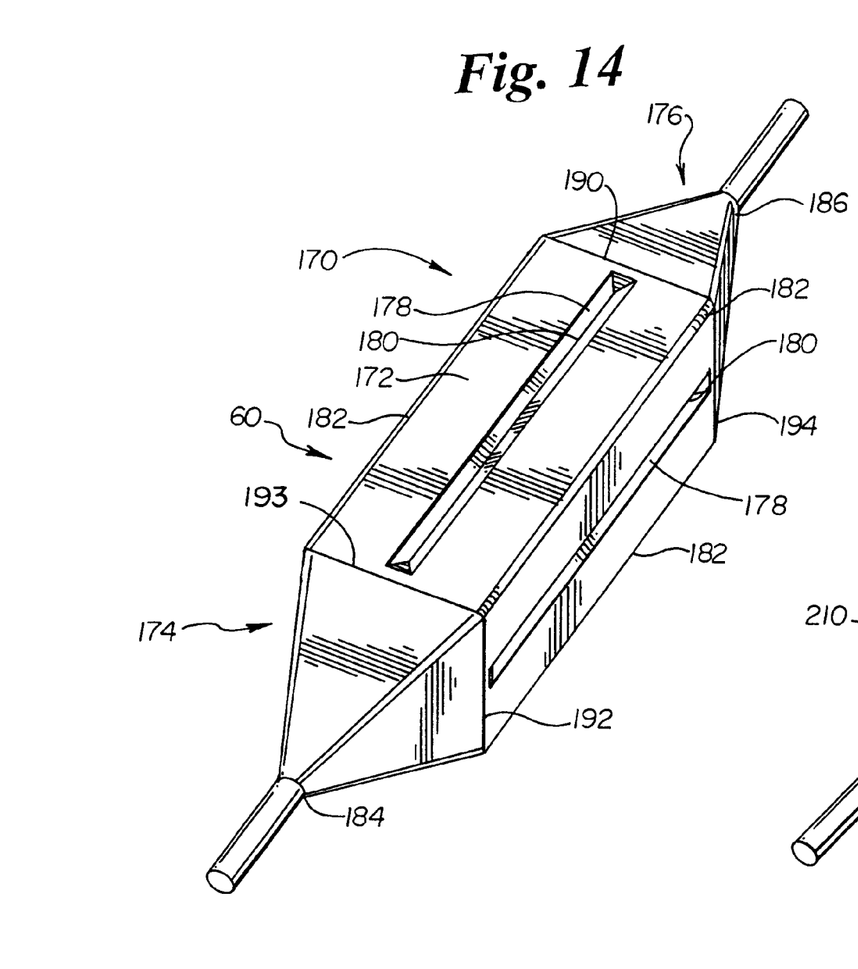
FIG. 14 is a perspective view of a third alternative embodiment of the present invention.

FIG. 14 is a perspective view of a third alternative embodiment of the present invention. FIG. 14 shows balloon 170 in a non-pressurized state 60. Balloon 170 has a body 172, a proximal transition region 174 and a distal transition region 176. Body 172 has triangular indentations 178. Triangular indentations 178 each have a crease 180. Longitudinal ribs 182 are shown in the third alternative embodiment as defining a beveled or rounded edge. The rounded edges define a radius at the edge of each fold when balloon 170 is quad-folded into the deflated state 28 to reduce trauma to the patient's vascular system by minimizing the balloon profile. In the third alternative embodiment, triangular indentations 178 are positioned within body 172, and creases 180 of triangular indentations 178 extend from a proximal end 193 of body 172 to a distal end 190 of body 172. Creases 180 of each of the number of triangular indentations 178 do not intersect perpendicular ribs 192 or perpendicular ribs 194. Creases 180 of each of the number of triangular indentations 178 enhance the collapse of balloon 170 from an expanded configuration or inflated state 30 to a folded configuration or deflated state 28 once the resistance of perpendicular ribs 192 and perpendicular ribs 194 to collapse has been overcome by extending creases 180 into proximal transition region 174 and distal transition region 176 to enhance or further induce the quad-folding of balloon 170.

Figure 15:
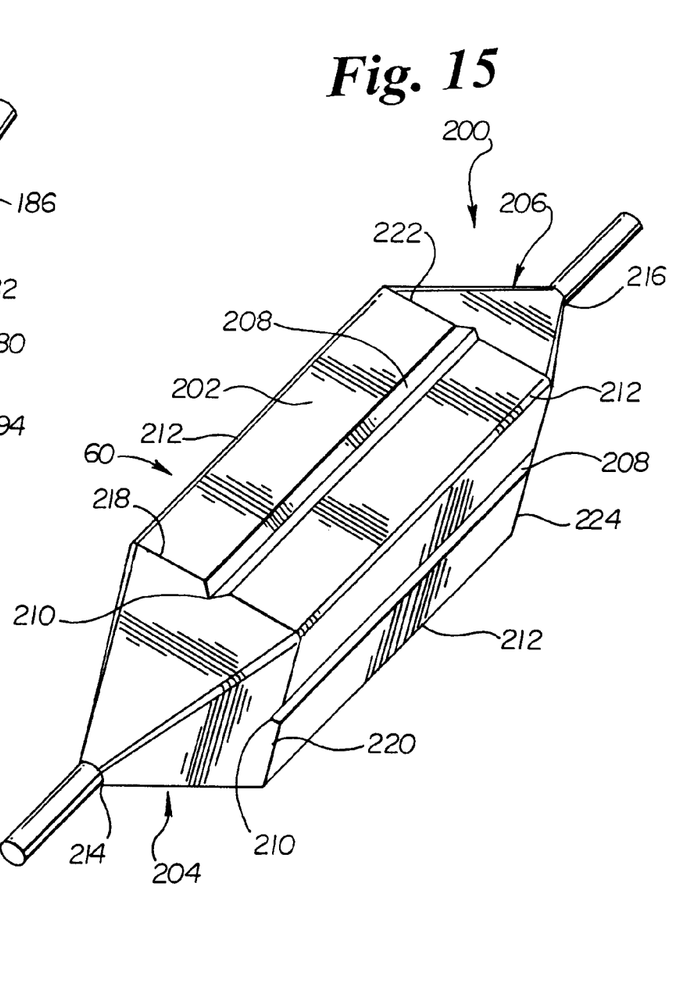
FIG. 15 is a perspective view of a fourth alternative embodiment of the present invention.

FIG. 15 is a perspective view of a fourth alternative embodiment of the present invention. FIG. 15 shows a balloon 200 having a body 202, a proximal transition region 204, and a distal transition region 206. Balloon 200 is in a non-pressurized state 60. Triangular indentations 208 have creases 210 and are positioned in body 202 of balloon 200 between longitudinal ribs 212. Longitudinal ribs 212 reduce patient trauma due to a radius which is located at the edge of each fold by minimizing the balloon profile when balloon 200 is in the deflated state 28. Longitudinal ribs 212 extend from proximal end 214 to distal end 216. Proximal end 218 of body 200 has perpendicular ribs 220. Distal end 222 of body 202 has perpendicular ribs 224. Creases 210 of triangular indentations 208 extend from proximal end 218 of body 202 to distal end 222 of body 202 and intersect perpendicular ribs 220 and perpendicular ribs 224 to reduce the resistance of perpendicular ribs 220 and perpendicular ribs 224 to collapse during deflation. Creases 210 of triangular indentations 208 enhance the collapse of balloon 200 from an expanded configuration or inflated state 30 to the quadra-folded configuration or the deflated state 28 once the resistance of perpendicular ribs 220 and perpendicular ribs 224 to collapse has been overcome during deflation.

Figure 16:
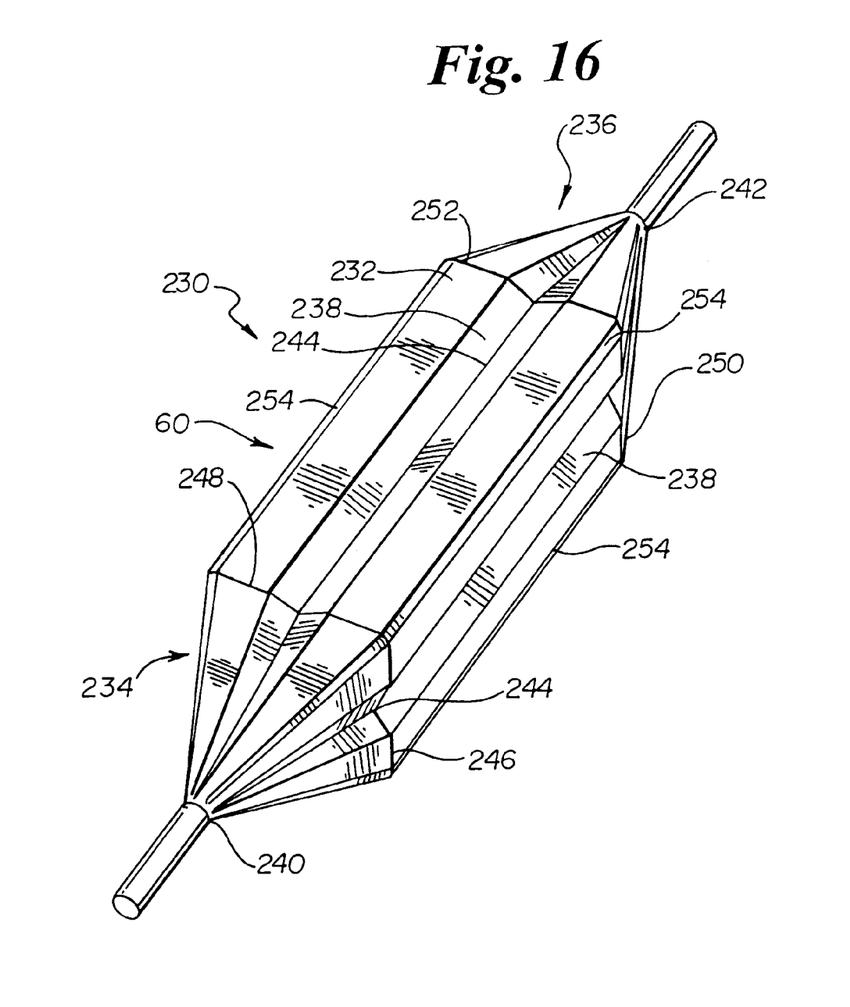
FIG. 16 is a perspective view of a fifth alternative embodiment of the present invention.

FIG. 16 is a perspective view of a fourth alternate embodiment of the present invention. FIG. 16 shows balloon 230 which has a body 232, a proximal transition region 234, and a distal transition region 236. Balloon 230 is in a non-pressurized state 60. Triangular indentations 238 extend from proximal end 240 to distal end 242. Triangular indentations 238 each have one of creases 244. Perpendicular ribs 246 are located at a proximal end 248 of body 232. Perpendicular ribs 250 are located at a distal end 252 of body 232. Longitudinal ribs 254 extend from proximal end 240 to distal end 242 of balloon 230. Triangular indentations 238 are equidistantly spaced between adjacent longitudinal ribs 254. Creases 244 of triangular indentations 238 extending from proximal end 240 to distal end 242 intersect perpendicular ribs 246 and perpendicular ribs 250 to reduce the resistance of perpendicular ribs 246 and perpendicular ribs 250 to collapse during deflation. Creases 244 of triangular indentations 238 enhance the collapse of balloon 230 from an expanded configuration or inflated state 30 to a quad-folded configuration or deflated state 28 once the resistance of perpendicular ribs 246 and perpendicular ribs 250 to collapse has been overcome during deflation of balloon 230.

Having thus described the preferred embodiments of the present invention, those of skill in the art will readily appreciate that yet other embodiments may be made and used within the scope of the claims hereto attached.

What is claimed:

1. A balloon for a catheter, comprising:
    a. an inflatable membrane formed of a flexible material defining an inflation chamber which is adapted for inflation from a folded configuration to an expanded configuration and deflation back to a folded configuration, said balloon having a longitudinal axis extending between a proximal and a distal end;
    b. a number of longitudinal ribs formed in said flexible material of said inflation chamber which extend longitudinally between said proximal and said distal end;
    c. a number of perpendicular ribs formed in said flexible material of said inflation chamber which extend between said number of longitudinal ribs, said number of perpendicular ribs being generally perpendicular to said longitudinal axis, said number of perpendicular ribs having a higher resistance to collapse during deflation; and d. a number of indentations formed in said flexible material of said inflation chamber, each indentation positioned between two adjacent ones of said number of longitudinal ribs and extending longitudinally at least a portion of the length between said proximal end and said distal end, said number of indentations enhancing said collapse of said inflation chamber from said expanded configuration to said folded configuration.

2. The balloon of claim 1 wherein said balloon comprises a reduced diameter proximal transition region adjacent said proximal end, a reduced diameter distal transition region adjacent said distal end, and a body positioned between said proximal transition region and said distal transition region.

3. The balloon of claim 2 wherein said number of perpendicular ribs comprises a first plurality of said number of perpendicular ribs positioned in a first plane perpendicular to said longitudinal axis, said first plurality of said number of perpendicular ribs joining said proximal transition region to said body, a second plurality of said number of perpendicular ribs positioned in a second plane perpendicular to said longitudinal axis, said second plurality of said number of perpendicular ribs joining said distal transition region to said body.

4. The balloon of claim 3 wherein each one of said number of indentations is an inwardly directed fold, said fold being directed towards said longitudinal axis and having a crease which extends generally longitudinally at a radial angle toward said longitudinal axis.

5. The balloon of claim 4 wherein a first portion of said number of indentations is positioned near said proximal end of said balloon, said crease of each one of said first portion of said number of indentations extending through a particular one of said first plurality of said number of perpendicular ribs, a second portion of said number indentations being positioned near said distal end of said balloon, said crease of each one of said second portion of said number of indentations extending through a particular one of said second plurality of said number of perpendicular ribs to reduce said higher resistance of said number of perpendicular ribs to collapse during deflation and enhancing said collapse of said inflation chamber from said expanded configuration to said folded configuration.

6. The balloon of claim 3 wherein said first plurality of said number of perpendicular ribs is four and said second plurality of said number of perpendicular ribs is four.

7. The balloon of claim 1 wherein said flexible material is formed of polyethylene terephthalate.

8. A balloon for a catheter, comprising:
a. an inflatable membrane for attachment to a catheter shaft for introduction into a human body conduit, said inflatable membrane formed of a flexible material defining an inflation chamber which is adapted for inflation from a folded configuration to an expanded configuration and deflation back to a folded configuration, said balloon having a longitudinal axis extending between a proximal and a distal end;
b. a number of ribs formed in said flexible material of said inflatable membrane, said number of ribs being equidistantly spaced and extending generally along said longitudinal axis; and
c. a number of folds formed in said flexible material of said inflatable membrane, each fold positioned between two adjacent ones of said number of ribs each fold extending longitudinally at least a portion of the length between said proximal end and said distal end of said balloon, said fold being inwardly directed towards said longitudinal axis and having a crease which extends generally longitudinally at a radial angle to said longitudinal axis.

9. The balloon of claim 8 wherein said number of ribs comprise a number of longitudinal ribs formed in said flexible material of said inflatable membrane which extend longitudinally between said proximal and said distal end.

10. The balloon of claim 9 wherein said balloon comprises a reduced diameter proximal transition region adjacent said proximal end, a reduced diameter distal transition region adjacent said distal end, and a body portion positioned between said proximal transition region and said distal transition region.

11. The balloon of claim 10 wherein said number of ribs further comprise a number of perpendicular ribs formed in said flexible material of said inflation chamber which intersect said number of longitudinal ribs, said number of perpendicular ribs being perpendicular to said longitudinal axis and having a higher resistance to collapse during deflation.

12. The balloon catheter of claim 11 wherein said number of perpendicular ribs comprise a first plurality of said number of perpendicular ribs positioned in a first plane perpendicular to said longitudinal axis, said first plurality of said number of perpendicular ribs joining said proximal transition region to said body, a second plurality of said number of perpendicular ribs positioned in a second plane perpendicular to said longitudinal axis, said second plurality of said number of perpendicular ribs joining said distal transition region to said body.

13. The balloon of claim 12 wherein a first portion of said number of folds is positioned near said proximal end of said balloon, each particular one of said first portion of said number of folds extending through a particular one of said first plurality of said number of perpendicular ribs, a second portion of said number of folds being positioned near said distal end of said balloon, each particular one of said second portion of said number of folds extending through a particular one of said second plurality of said number of perpendicular ribs to enhance said collapse of said inflation chamber from said expanded configuration to said folded configuration.

14. The catheter of claim 9 wherein said number of longitudinal ribs is four.

15. The balloon of claim 8 wherein said flexible material is polyethylene terephthalate.

16. The balloon of claim 12 wherein said first plurality of said number of perpendicular ribs is four and said second plurality of said number of perpendicular ribs is four.

* * * * *